US012714406B2

(12) United States Patent
Hendricks

(10) Patent No.: US 12,714,406 B2
(45) Date of Patent: Aug. 25, 2026

(54) COLLECTION CONTAINER

(71) Applicant: MYMED DEVICES, LLC, Canton, OH (US)

(72) Inventor: Sebastian S. Hendricks, Canton, OH (US)

(73) Assignee: MYMED DEVICES, LLC, Canton, OH (US)

( * ) Notice: Subject to any disclaimer, the term of this patent is extended or adjusted under 35 U.S.C. 154(b) by 102 days.

(21) Appl. No.: 18/776,661

(22) Filed: Jul. 18, 2024

(65) Prior Publication Data

US 2024/0366195 A1 Nov. 7, 2024

Related U.S. Application Data

(63) Continuation-in-part of application No. 17/990,326, filed on Nov. 18, 2022, which is a continuation of application No. 17/837,687, filed on Jun. 10, 2022, now abandoned.

(60) Provisional application No. 63/243,293, filed on Sep. 13, 2021, provisional application No. 63/209,119, filed on Jun. 10, 2021.

(51) Int. Cl.

| | |
|---|---|
| ***A61B 10/00*** | (2006.01) |
| ***A47K 7/08*** | (2006.01) |
| ***A47K 13/30*** | (2006.01) |

(52) U.S. Cl.
CPC .......... *A61B 10/007* (2013.01); *A47K 13/302* (2013.01); *A61B 10/0038* (2013.01); *A47K 7/08* (2013.01)

(58) Field of Classification Search
CPC ......................... A61B 10/007; A61B 10/0038; A47K 13/302; A47K 7/08
See application file for complete search history.

(56) References Cited

U.S. PATENT DOCUMENTS

| | | | |
|---|---|---|---|
| 5,149,506 | A | 9/1992 | Skiba et al. |
| D489,453 | S | 5/2004 | Sapyta |

(Continued)

FOREIGN PATENT DOCUMENTS

| | | | |
|---|---|---|---|
| CN | 210533777 | U | 5/2020 |
| GB | 2576743 | A | 3/2020 |
| JP | 3228377 | U | 10/2020 |

OTHER PUBLICATIONS

Avantor/ TheraPak Stool Sample Instructions—StoolSample_ Instructions.pdf (aruplab.com).

(Continued)

*Primary Examiner* — Christine J Skubinna
(74) *Attorney, Agent, or Firm* — Jacob M. Ward; Ward Law Office LLC

(57) ABSTRACT

A collection container can include a first end, a second end, and a central recess disposed between the first end and the second end. The central recess can be configured to receive a sample. The collection container can have a first stopper disposed adjacent to the first end and a second stopper disposed adjacent to the second end. The first stopper and the second stopper can be configured to together grasp opposite sides of a toilet bowl upon installation of the collection container on the toilet bowl. The first stopper and the second stopper selectively hold the collection container in place on the toilet bowl during collection of the sample.

15 Claims, 14 Drawing Sheets

(56) References Cited

U.S. PATENT DOCUMENTS

| | | | | |
|---|---|---|---|---|
| 7,300,627 | B1 * | 11/2007 | Sun .................... | A61B 10/0045 422/417 |
| 8,079,562 | B1 * | 12/2011 | Denman .............. | A61B 10/007 4/144.1 |
| 8,615,824 | B2 | 12/2013 | Sonderholm et al. | |
| 9,176,026 | B2 | 11/2015 | Sidorsky et al. | |
| 10,130,293 | B2 * | 11/2018 | Hidas ................... | A61B 5/6887 |
| 2006/0184064 | A1 | 8/2006 | Paasch et al. | |
| 2012/0316462 | A1 * | 12/2012 | Enos .................. | A61B 10/0038 600/562 |
| 2014/0017720 | A1 | 1/2014 | Sidorsky et al. | |
| 2014/0329273 | A1 * | 11/2014 | Fiedler ............... | A61B 10/0038 435/309.1 |
| 2018/0008238 | A1 | 1/2018 | Paige | |
| 2018/0317892 | A1 | 11/2018 | Catlin | |

OTHER PUBLICATIONS

GP Medical Devices Easy Sampler Series—The EasySampler series of disposable products for collecting stool and urine specimens (gpmedicaldevices.co.uk).

Takahashi Keisei Corp. Stool Sample Collection Sheet—Amazon.com: Raku-Ryu Cup flushable Stool Sample Collection Sheet (Pack of 5) : Health & Household.

* cited by examiner

FROM FIG. 13A
REMOVING PORTION OF SAMPLE FROM COLLECTION CONTAINER
312
RAISING TOILET SEAT
314
REMOVING COLLECTION CONTAINER FROM TOILET BOWL
316
DISPOSING OF REMAINING SAMPLE
318
CLEANING COLLECTION CONTAINER
320

100'

100'

COLLECTION CONTAINER

CROSS-REFERENCE TO RELATED APPLICATIONS

This application is a continuation-in-part application of U.S. Utility application Ser. No. 17/990,326 filed Nov. 18, 2022, which claims the benefit of U.S. Utility application Ser. No. 17/837,687 filed Jun. 10, 2022, and claims the benefit of U.S. Provisional Application No. 63/243,293 filed on Sep. 13, 2021, and U.S. Provisional Application No. 63/209,119, filed on Jun. 10, 2021. The entire disclosures of the above applications are incorporated herein by reference.

FIELD

The present technology relates to collecting samples of soft matter compositions, including devices and methods for collecting stool and urine samples.

INTRODUCTION

This section provides background information related to the present disclosure which is not necessarily prior art.

Stool and urine sample collection and subsequent handling for patients as ordered by physicians for diagnostics can be a tedious, messy, and highly unpleasant process for patients. The vast amount of stool sample collections by patients are completed in the home and subsequently processed in a lab or diagnostic facility. Perhaps the most unpleasant aspect for patients is the handling required to transfer stool samples into a collection cup. As a result of these unpleasant aspects, many patients decide not to submit their stool samples in compliance with doctor's orders.

After their clinician has ordered a stool sample, the patient may be provided with a stool sample a collection device, supplied by the diagnostic center or by their doctor's office or may procure a collection device themselves. It is common for patients who must repeatedly provide stool samples to purchase a pack of several collection devices or a more sustainable reusable collection device.

There are multiple steps in collecting a sample, starting with the patient sitting atop a collection device fastened to their toilet or where the patient situates themselves above a paper drape or collection cup designed to catch the sample and prevent it from falling into the toilet bowl. After the patient has deposited their sample into the collection cup or drape, they are required to wear plastic gloves and use a tool, such as a tongue depressor or a small, plastic spoon, to collect measured samples from the collection device. The patient is then required to use the tool to distribute these smaller samples into a variety of containers, jars, tubes, and other collection receptacles provided to collect, store, and transport the samples. Some of the tubes are bio-assay tubes with liquid (buffer solution or formalin) dedicated for diagnostic technologies or methods such as PCR (polymerase chain reaction) systems, stool cultures, PCR multiplexing systems, bio-assays, and next generation genome/DNA sequencing technologies used to identify genetic bio-markers for specific pathogens in the sample.

After distributing the measured samples into the various collection jars and tubes, the patient may be required to refrigerate and/or freeze the samples to limit contamination and maintain viability of the samples. The significant handling required to distribute smaller sample quantities along with the sight and odor of the sample contribute to an undignified patient experience. Patient compliance (adherence to sample submission) suffers as a result of this unpleasant, messy process. A patient's reticence to complete the sample collection and handling process significantly reduces sample submission to labs for testing. The resultant absence of diagnostic results can hinder a clinician's ability to diagnose and treat their patient.

There are various collection devices designed solely for sample collection. These simple collection devices include paper or flexible plastic sheets that are draped over a toilet lid to "catch" the sample. These methods expose the sample and patient to contaminants and require the patient to handle their sample with a stick or a spoon to distribute measured samples into various other collections jars. Further, these collection means are typically clumsy and flimsy resulting in the sample being spilled and wasted.

Alternatively, there are a variety of stool sample collection devices that enable a patient to collect and store their stool sample generally for the purpose of transporting whole specimens. Many of these devices employ toilet brackets or frames that are secured under the toilet seat and situated over the toilet bowl. Most of these brackets are secured under the toilet seat lid using adhesive strips, non-slip surfaces and adjustable clamps. The majority of these collection and transport containers come equipped with a threaded cap that is fastened to the container after collection in order to prepare it for transport to the lab or shipping. These in-toilet collection devices still require a patient to deposit their sample into a single jar or rigid container designed only for transport or storage. If the patient is required to distribute measured samples from these collection devices, the patient must manually scoop smaller samples (again, typically using wooden tongue depressors) into additional tubes and containers.

These various devices are sufficient to collect, contain and transport stool samples, However, they do not substantially or successfully mitigate some of the common factors (such as handling and dispensing) that patients find so unpleasant when submitting a stool sample for diagnostic purposes. While various stool collection methods partially reduce the unpleasant nature of stool sample collection and transport, they are not specifically designed to mitigate direct handling and do not have specific features that allow patients or lab technicians to dispense measured samples without direct handling. Without a dedicated disbursement element or a feature to distribute sample quantities from the full sample, patient compliance will continue to present a challenge to clinicians and diagnostic centers. Alternatively, an easy method is dispensing measured samples which may also be a safer and more expedient process for lab technicians and clinicians who may need to dispense smaller sample quantities themselves.

No current collection device provides patients with a fully integrated system for collection, containment, and dispensing (alternatively: "disbursement") of measured (alternatively: "a portion of the whole sample") stool samples for clinical diagnostic applications. Accordingly, a long-felt and yet unmet need exists to change this dynamic for stool samples provided by patients for diagnostic testing. There is a need for a system that facilitates easier stool collection by a patient, protects the sample from bio-contamination, and enables easier sample disbursement into collection receptacles by a patient or lab technician. This methodology can play a critical role in improving patient compliance and making diagnostic data more readily available for patients, diagnostic centers, clinicians, and labs.

SUMMARY

In concordance with the instant disclosure, a system that facilitates easier stool collection by a patient, protects the sample from bio-contamination, and enables easier sample disbursement into collection receptacles by a patient or lab technician, has surprisingly been discovered.

The present technology optimizes sample collection, including ways to collect stool samples in a container.

In one embodiment, a collection container can have a first end, a second end, and a central recess disposed between the first end and the second end. The central recess can be configured to receive a sample. A first stopper disposed adjacent to the first end and a second stopper disposed adjacent to the second end. The first stopper and the second stopper can be configured to together grasp opposite sides of a toilet bowl upon installation of the collection container on the toilet bowl. The first stopper and the second stopper selectively hold the collection container in place on the toilet bowl during collection of the sample.

In another embodiment, a sample collection kit is disclosed. The sample collection kit can have a collection container and a collection cup. The collection container can include a first end, a second end, and a central recess disposed between the first end and the second end. The central recess can be configured to receive a sample. A first stopper disposed adjacent to the first end and a second stopper disposed adjacent to the second end. The first stopper and the second stopper can be configured to together grasp opposite sides of a toilet bowl upon installation of the collection container on the toilet bowl. The first stopper and the second stopper selectively hold the collection container in place on the toilet bowl during collection of the sample. The collection cup can have a primary body and a lid. The lid can have a deep scoop depending from an inner surface of the lid. The deep scoop can be configured to be inserted into the central recess of the collection container.

In yet another embodiment, a method of collecting a sample can include first providing a toilet. A collection container can also be provided. The collection container can have a first end, a second end, and a central recess disposed between the first end and the second end. The central recess can be configured to receive a sample. A first stopper disposed adjacent to the first end and a second stopper disposed adjacent to the second end. The first stopper and the second stopper can be configured to together grasp opposite sides of a toilet bowl upon installation of the collection container on the toilet bowl. The first stopper and the second stopper selectively hold the collection container in place on the toilet bowl during collection of the sample. The collection container can be disposed on the toilet bowl, whereby the first stopper and the second stopper grasp opposite sides of the toilet bowl. The sample can then be received in the collection container. A portion of the sample can then be removed from the collection container, whereby the sample is collected.

In a further embodiment, the collection container can be particularly configured as a stool specimen collection container. The collection container can be placed under a seat of a toilet and can be positioned at a front end of the toilet. A main hole of the collection container can be centralized over a hole of the toilet, where one or more hollow stoppers are placed along outside edges of the toilet. A pour spout can be positioned to have space between the pour spout and a front, inner wall of the toilet. In this way, male body parts can be positioned on the pour spout allowing for easy urination if only a stool sample is to be collected by the collection container. If urine is also to be collected, the urine can be collected in the main hole along with the stool. The urine can be poured into a measurement container for testing. Stool can be removed and placed into the same or another measurement container, using a perforated spoon, for example.

The collection container can be used as follows. The toilet lid can be lifted. The collection container can be placed flat over a main hole of the toilet, where hollow stoppers can be placed on the outside of the toilet. The collection container can be positioned towards the center of the toilet. The toilet lid can then be closed. The user can then sit down on the toilet. The user can then deposit their sample in the collection container. The user can then wipe as needed and drop the toilet paper outside of the collection container but still within the toilet bowl. The user can then stand up and lift the toilet lid. The user can pick up the collection container by a handle and remove the collection container from the toilet. The user can use a collection cup lid with a deep scoop to scoop the sample from the collection container. The collection cup lid can then be screwed onto a collection cup primary body. The user can dump any sample remaining in the collection container into the toilet and flush. The collection container may then be cleaned to be used subsequently.

The collection container can provide certain benefits and advantages. One such advantage relates to the pour spout. The pour spout can be at an acute angle instead of a small indent that can facilitate with pouring liquids more accurately and with less mess. Another advantage relates to the stoppers. The stoppers can militate against the collection container from shifting or moving during use. The stoppers also aid with the stability of the collection container when on the toilet and can reduce the number of spills or accidents. Finally, the stoppers can allow for easy stacking of at least two collection containers during storage. The handle of the collection container also provides an advantage in that it can allow the collection container to be easily picked up and set down. The handle can also provide a better grip when cleaning the collection container.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

DETAILED DESCRIPTION

Figure 1:
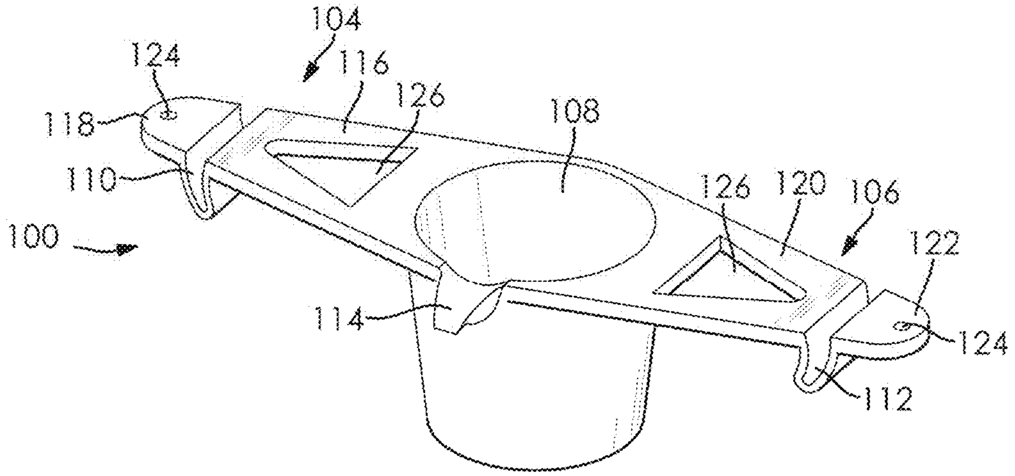
FIG. 1 is a top perspective view of a collection container.
Figure 2:
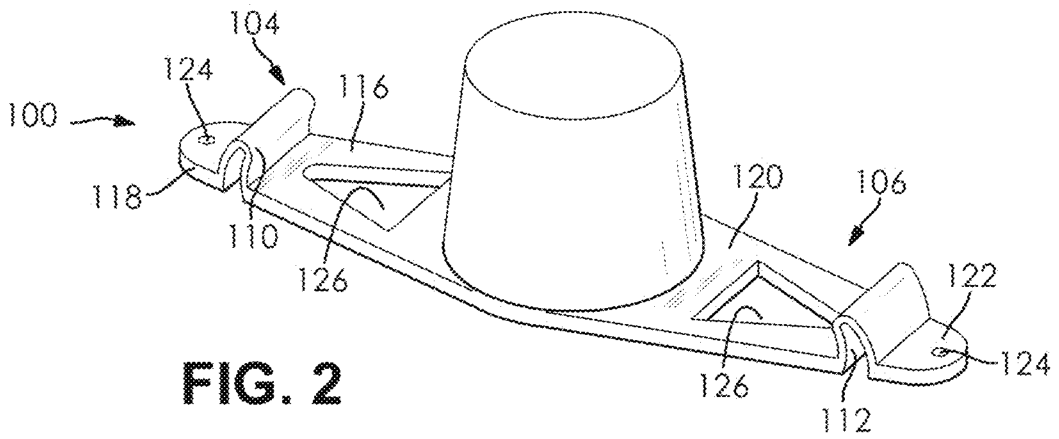
FIG. 2 is a bottom perspective view thereof.

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology relates to a collection container 100, sample collection kit 200, and method 300 for collecting a sample, shown generally in the accompanying figures.

As shown in FIGS. 1-8, a collection container 100 can include a first end 104, a second end 106, and a central recess 108 disposed between the first end 104 and the second end 106. The central recess 108 can be configured to receive a sample 101. The collection container 100 can have a first stopper 110 disposed adjacent to the first end 104 and a second stopper 112 disposed adjacent to the second end 106. The first stopper 110 and the second stopper 112 can be configured to together grasp opposite sides of a toilet bowl 103 upon installation of the collection container 100 on the toilet bowl 103. The first stopper 110 and the second stopper 112 can selectively hold the collection container 100 in place on the toilet bowl 103 during collection of the sample 101.

Figure 6:
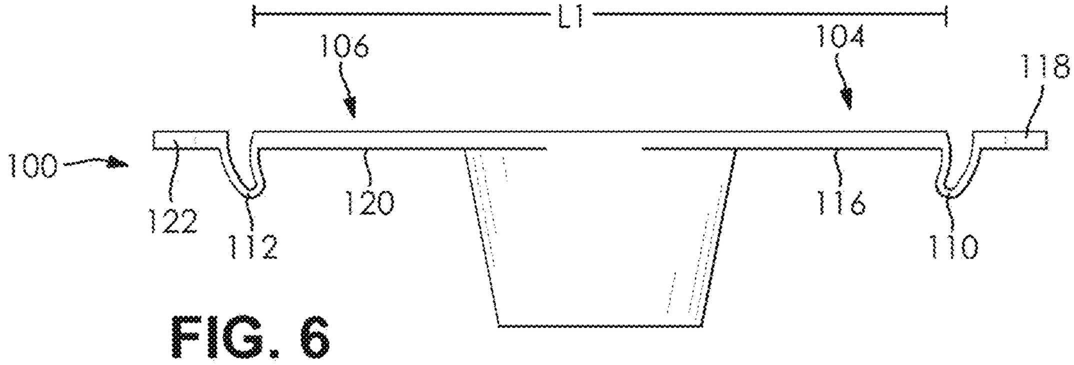
FIG. 6 is a rear elevational view thereof.
Figure 9:
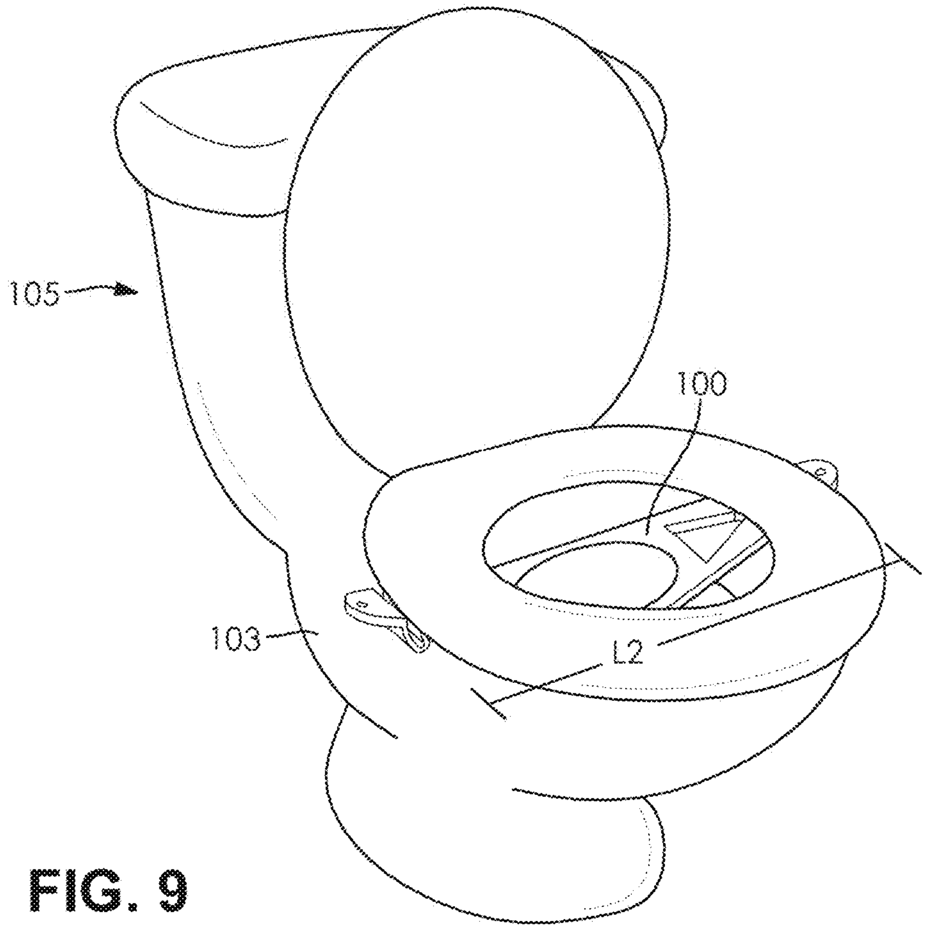
FIG. 9 is a top perspective view of the collection container coupled to a toilet, in accordance with the present disclosure.

The first stopper 110 and the second stopper 112 can be spaced apart on the collection container by a length (L1), as shown in FIG. 6. The toilet bowl 103 can have a length (L2), as shown in FIG. 9. The length (L1) can be substantially similar to the length (L2) across the outer rim of the toilet bowl 103. The length (L1) can be substantially similar to the length (L2) of the toilet bowl such that the first stopper 110 and the second stopper 112 together grasp opposite sides of a toilet bowl 103 upon installation of the collection container 100. Advantageously, this can militate against the collection container 100 from moving while in use on the toilet bowl 103.

Figure 7:
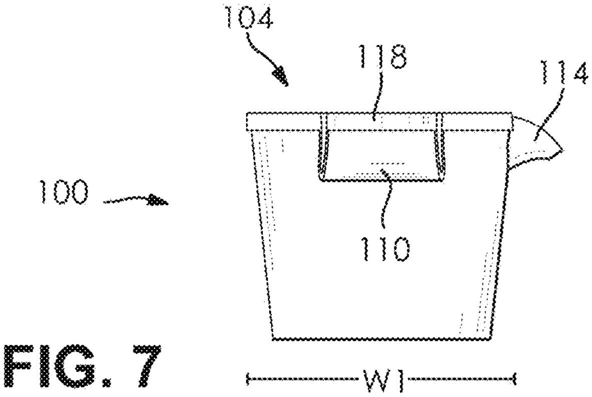
FIG. 7 is a left side elevational view thereof.

The collection container 100 can also have a width W1, as shown in FIG. 7. The width W1 can be such that the collection container 100 can sit within the toilet bowl 103. The width W1 can smaller than the width of the toilet bowl such that the user may dispose of toilet paper within the gaps between the collection container 100 and the toilet bowl 103 and allow the toilet paper to fall into the toilet bowl 103. Advantageously, this can allow the user to clean themselves and dispose of the toilet paper without waiting until they have removed the collection container 100 from the toilet bowl 103.

The collection container 100 can be a unitary piece. The unitary collection container 100 can provide support when the collection container 100 is in use by militating against the collection container 100 drooping into the toilet bowl 103 when the user is depositing a sample 101 in the collection container 100. The unitary collection container 100 can also allow for an easier clean up process. The user must only clean one piece instead of having to deconstruct a multi-piece collection container, clean each individual piece, and reassemble the multi-piece collection container.

The collection container 100 can be formed from a rigid material. The rigid material can allow for the collection container 100 to stay in place while in use and militate against the collection container 100 drooping into the toilet bowl. Additionally, the rigid material can be non-porous. The non-porous nature of the material can allow for easy clean up and sterilization. The non-porous material can also militate against the spread of disease and cross contamination by reducing the amount of sample 101 that remains on the collection container 100 after each use. As a non-limiting examples, the collection container 100 can be formed from polyvinyl chloride (PVC), polyethylene terephthalate glycol (PETG), high density polyethylene (HDPE), polystyrene, acrylic, and/or vinyl. In a particular embodiment, the collection container 100 can be formed from polypropylene. One of ordinary skill in the art can select other suitable materials for forming the collection container 100 within the scope of the present disclosure.

Figure 3:
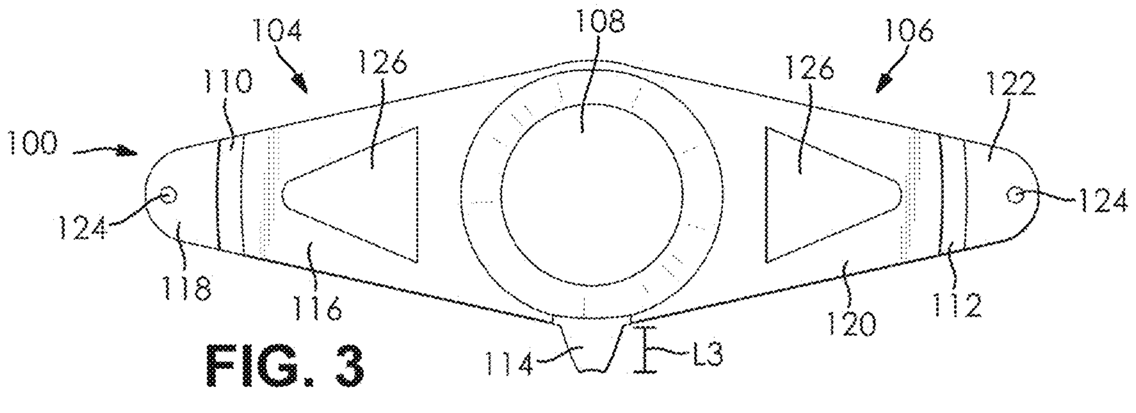
FIG. 3 is a top plan view thereof.
Figure 4:
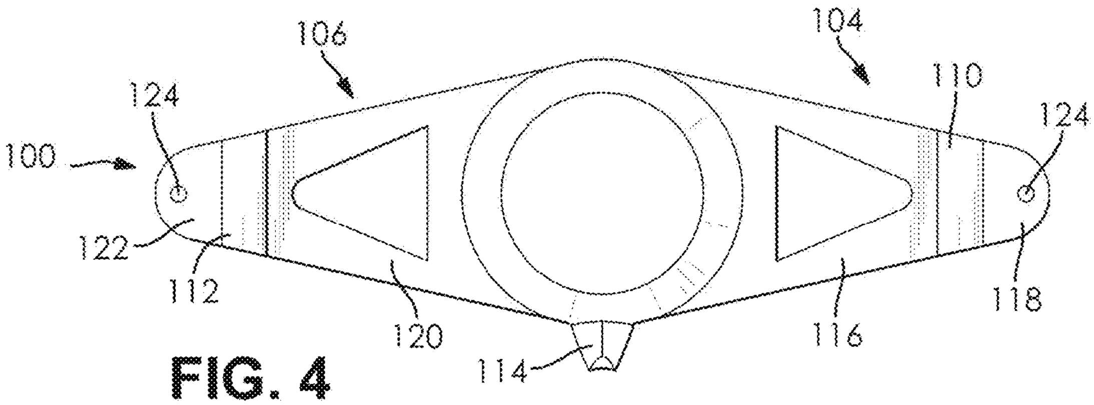
FIG. 4 is a bottom plan view thereof.
Figure 5:
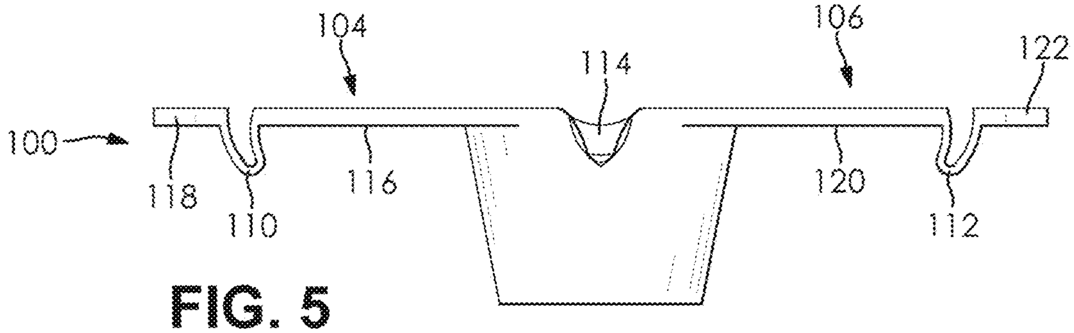
FIG. 5 is a front elevational view thereof.

With reference to FIG. 3, the central recess 108 can have a pour spout 114 with a pour spout length (L3). Advantageously, the pour spout 114 can militate against spillage while pouring a liquid sample 101 into a collection cup. The pour spout 114 can also militate against spillage during the cleaning of the collection container 100 by allowing the user to direct a stream of liquid. The pour spout length (L3) can be selected to allow the collection container 100 to sit within the toilet bowl 103. The pour spout length (L3) can be selected to allow for a gap between the pour spout 114 and the front of the toilet bowl 103 such that the user may dispose of toilet paper within the gap and allow the toilet paper to fall into the toilet bowl 103. Advantageously, this can allow the user to clean themselves and dispose of the toilet paper in the toilet bowl 103 without waiting until they have removed the collection container 100 from the toilet bowl 103. One of ordinary skill in the art can select a suitable pour spout length (L3).

As shown in FIGS. 1-7 the first end 104 of the collection container 100 can have a first arm 116. The first arm 116 can further include a first handle 118. The first stopper 110 can be located on the collection container 100 between the central recess 108 and the first handle 118. The second end 106 of the collection container 100 can have a second arm 120. The second arm 120 can further include a second handle 122. The second stopper 112 can be located on the collection container 100 between the central recess 108 and the second handle 122. As a non-limiting example, each of the first handle 118 and the second handle 122 can be rounded. Advantageously, the rounded nature of each of the first handle 118 and the second handle 122 can allow for a better grip of the collection container 100 during placement on the toilet bowl 103, removal from the toilet bowl 103, and during the cleaning process. Further, each of the first handle 118 and the second handle 122 can have a hole 124 configured to hang the collection container 100. Desirably, the hole 124 can allow the collection container 100 to hang for storage purposes as well as to hang to dry after the collection container 100 has been cleaned.

As shown in FIGS. 1-7, the first arm 116 and the second arm 120 can be disposed in the same plane as the central recess 108. Advantageously, the planar feature can allow the collection container 100 to sit closer to the user and militate against the sample 101 splashing up onto the user.

Figure 8:
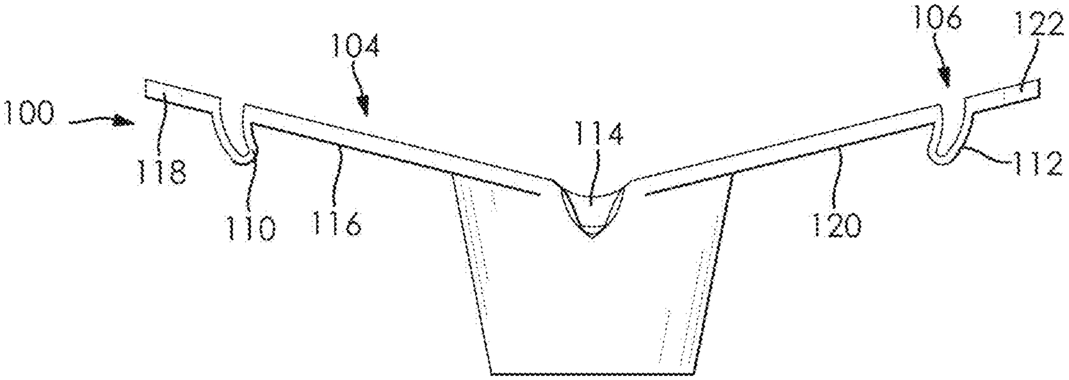
FIG. 8 is a front elevational view of the collection container according to one embodiment of the present disclosure.

In another embodiment shown in FIG. 8, each of the first arm 116 and the second arm 120 can be tapered toward the central recess 108. Advantageously, the tapering feature can allow the collection container 100 to sit flush with the rim of the toilet and militate against the toilet seat sitting awkwardly against the collection container 100 while in use. One of ordinary skill in the art can also select the suitable angle at which the first arm 116 and the second arm 120 taper toward the central recess 108.

As shown in FIGS. 1-8, the first stopper 110 and second stopper 112 can be hollow. Desirably, hollow stoppers can allow the collection container 100 to stack easily during transport and storage. Further, the first stopper 110 and the second stopper 112 can be curved toward the central recess 108. The first stopper 110 and second stopper 112 can have an arcuate surface with a curvature configured to match the curvature of the toilet bowl 103. The matching curvature of the arcuate surface of each of the first stopper 110 and the second stopper 112 and the toilet bowl 103 can facilitate a more secure connection between each of the first stopper 110 and the second stopper 112 and the toilet. Advantageously, the secure connection helps the collection container 100 remain in place on the toilet while in use further militating against possible mess. One of ordinary skill in the art can select a suitable curvature to match the curvature of the toilet bowl 103.

The first end 104 and the second end 106 can have one or more apertures formed therein, such as triangular cut outs 126 as shown in FIGS. 1-4. The triangular cut outs 126 can allow the collection container 100 to be manufactured using less material. The triangular cut outs 126 can also allow the collection container 100 to be lighter and therefore easier to maneuver while placing on the toilet and while cleaning. One of ordinary skill in the art can select the suitable area of the triangular cut outs 126.

Figure 10:
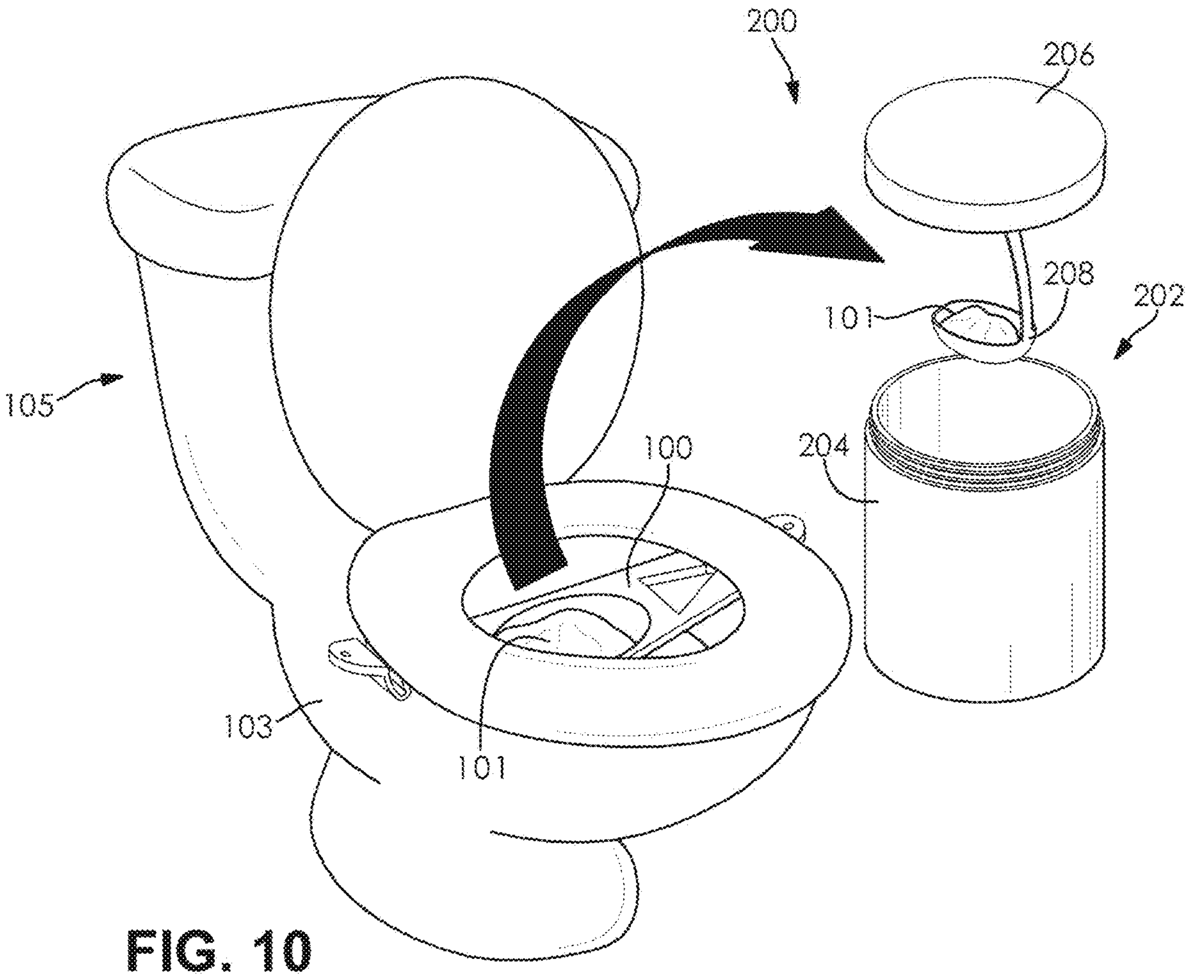
FIG. 10 is a top perspective view of the collection container coupled to the toilet and a collection cup scooping a sample from the collection container, in accordance with the present disclosure.
Figure 11:
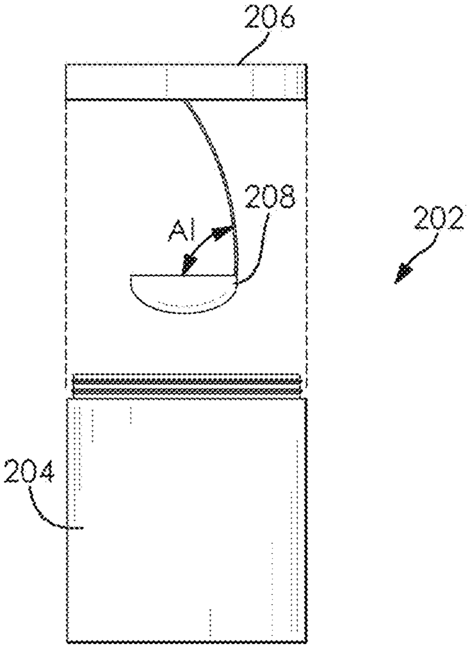
FIG. 11 is a left side elevational view of the collection cup.
Figure 12:
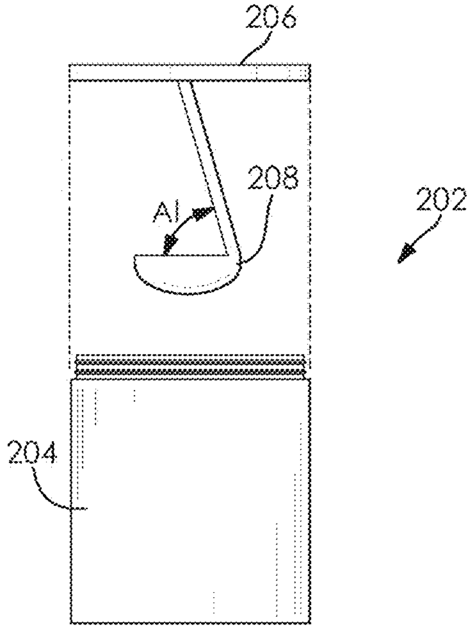
FIG. 12 is a left side elevational view of the collection cup according to one embodiment of the present disclosure.

The present disclosure also contemplates a sample collection kit 200, as shown in FIG. 10. The sample collection kit 200 can include the collection container 100, as described hereinabove. The sample collection kit 200 can further include a collection cup 202. The collection cup 202 can have a cup body 204 and a lid 206. The lid 206 can have a scoop 208 depending from an inner surface of the lid 206. The scoop 208 can be configured to be inserted into the central recess 108 of the collection container 100 for the collecting of a sample 101. The scoop 208 can have a wall of a height that is at least half the width of the scoop. The scoop 208 can allow the user to easily scoop their sample 101 and subsequently hold the sample 101 in the scoop 208 while the lid 206 is attached to the cup body 204. The scoop 208 can have an inner angle (A1) of about 90 degrees or less, shown in FIGS. 11-12. Advantageously, the scoop 208 can hold the sample 101 during transport to allow the sample 101 to be easily removed from the collection cup 202.

The sample collection kit 200 can also include a set of plastic gloves (not shown) to keep the user clean during use and prevent contamination or the spread of infection. Further, the sample collection kit 200 can include a means for cleaning the surface of the collection container 100, such as one or more alcohol towelettes, that can be employed before and after each use.

Figure 13A:
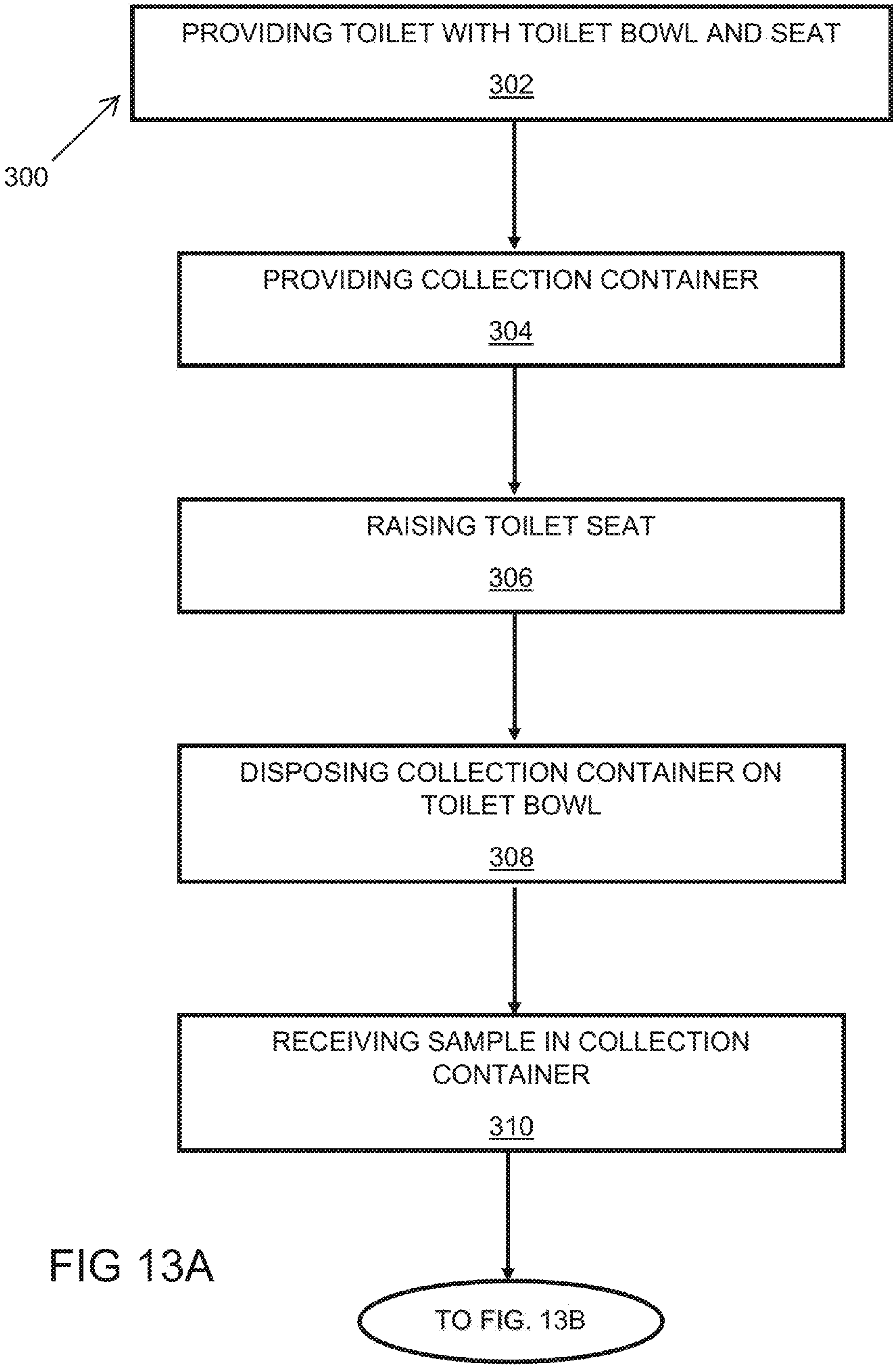
FIGS. 13A and 13B are a flow diagram illustrating a method of collecting the sample.
Figure 13B:
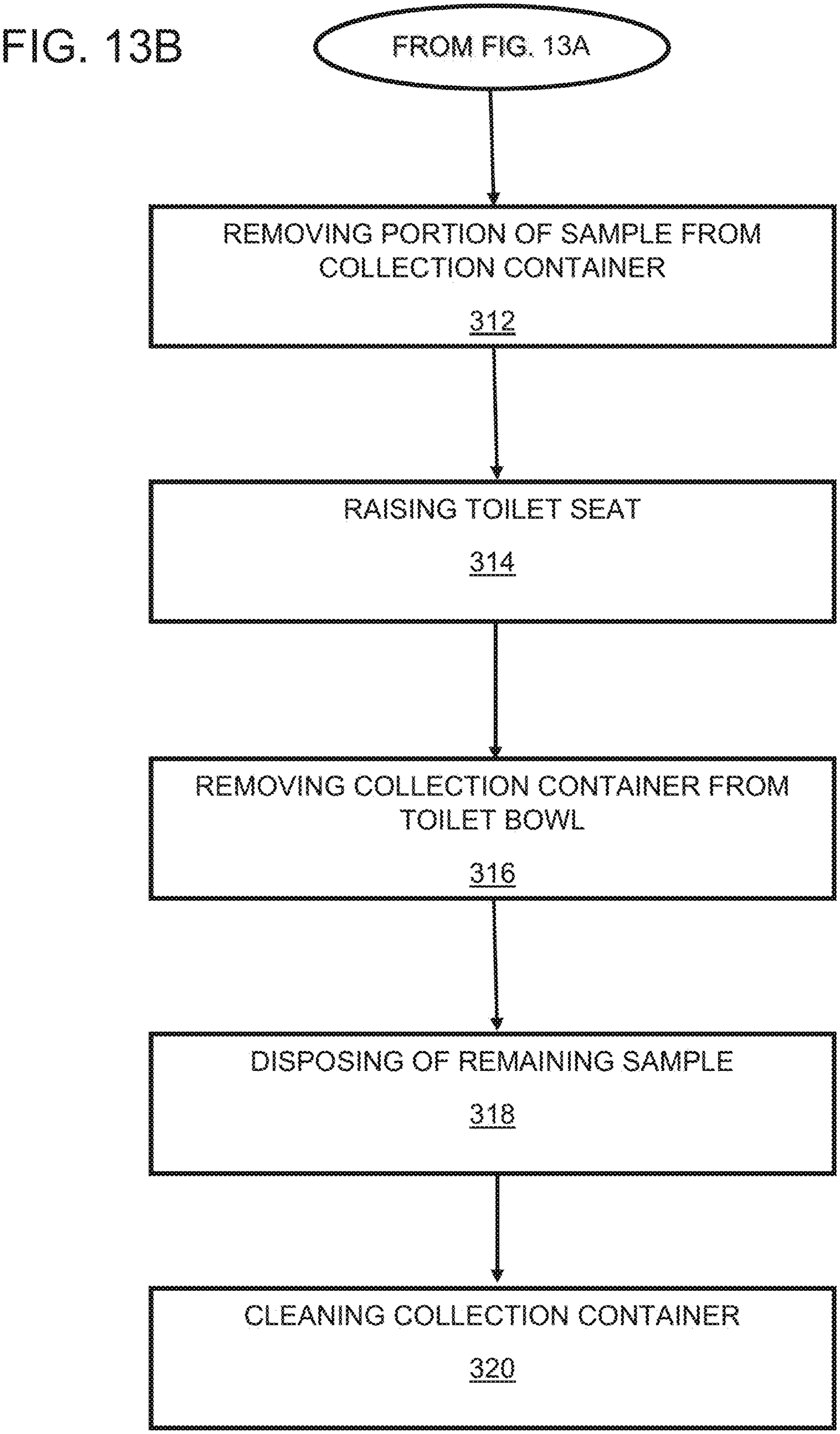
Figure 14:
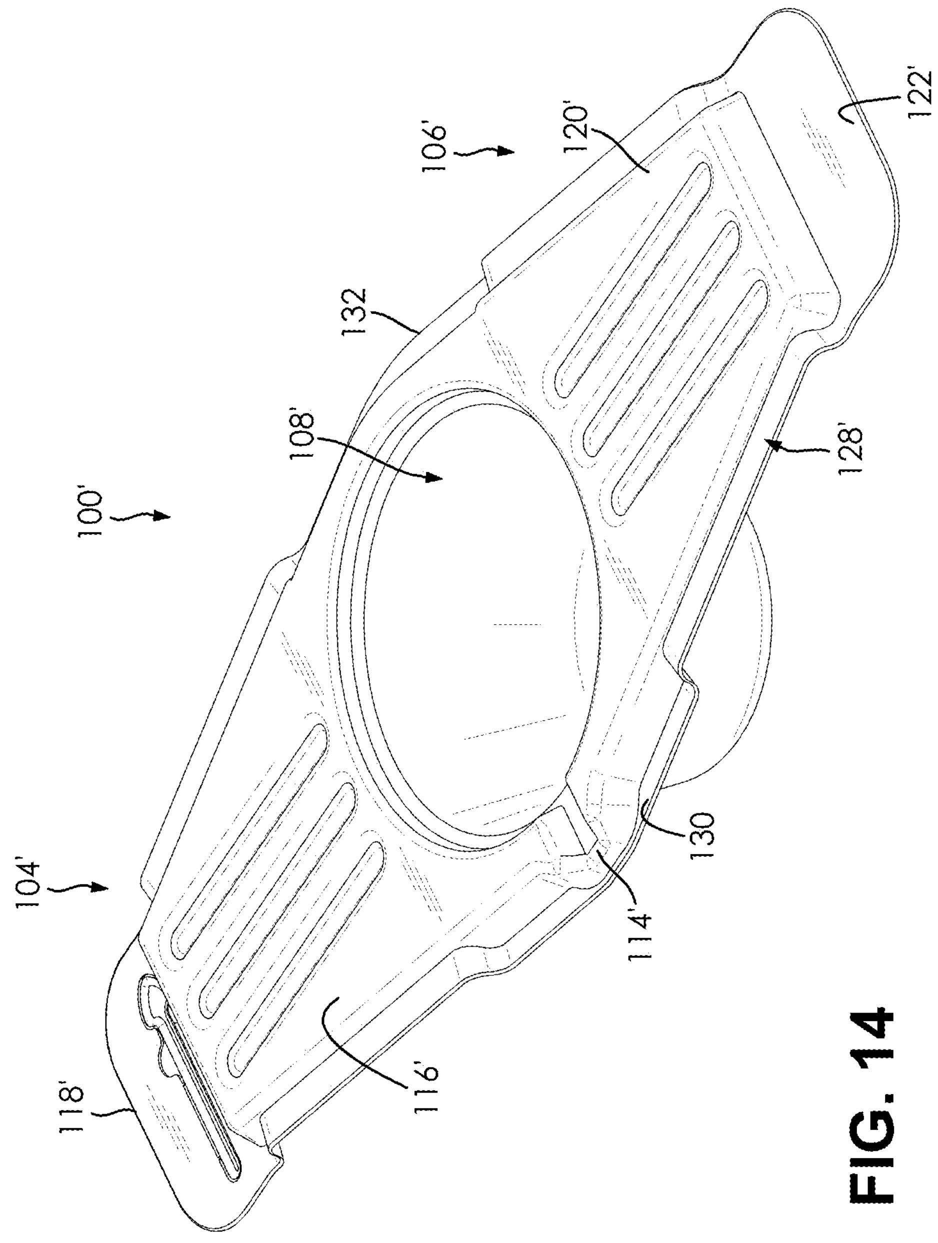
FIG. 14 is a top perspective view of a collection container with scoop.

This present disclosure further contemplates a method 300 of collecting a sample 101, shown in FIGS. 13A and 13B. In a first step 302, a toilet with a toilet bowl 103 and toilet seat can be provided. A collection container 100, as described hereinabove, can be provided in a second step 304. In a third step 306, the toilet seat can be raised to allow the collection container 100 to be disposed on the toilet bowl 103. In a fourth step 308, the collection container 100 can be disposed on the toilet bowl 103, whereby the first stopper 110 and the second stopper 112 together grasp opposite sides of the toilet bowl 103. The sample 101 is then received in the collection container 100 in a fifth step 310. In a sixth step 312, at least a portion of the sample 101 is removed from the collection container 100 by a collection receptable, and the sample 101 is therefore collected. In a seventh step 314, the user can raise the toilet seat. The user can then remove the collection container 100 from the toilet bowl 103, in an eighth step 316. In a ninth step 318, the user can dispose of any sample 101 remaining in the collection container 100. The user can then clean the collection container and store away for repeated use in a tenth step 320. The collection receptable used in the method 300 can be a collection cup 202, as described herein. The method 300 can further comprise a step 322 of scooping the sample 101 with the scoop 208 out of the collection container 100.

With reference to FIGS. 14-22, an additional embodiment of the collection container 100 is shown. The collection container 100' can be a unitary body. The collection container 100' can include the first end 104', the second end 106', and the central recess 108'. The first end 104' of the collection container 100' can have the first arm 116'. The first arm 116' can further include a first handle 118'. A first stopper 110' can be located on the collection container 100 between the central recess 108 and the first handle 118'. The second end 106' of the collection container 100 can have a second arm 120. The second arm 120' can further include the second handle 122'. The second stopper 112' can be located on the collection container 100' between the central recess 108 and the second handle 122'.

Figure 16:
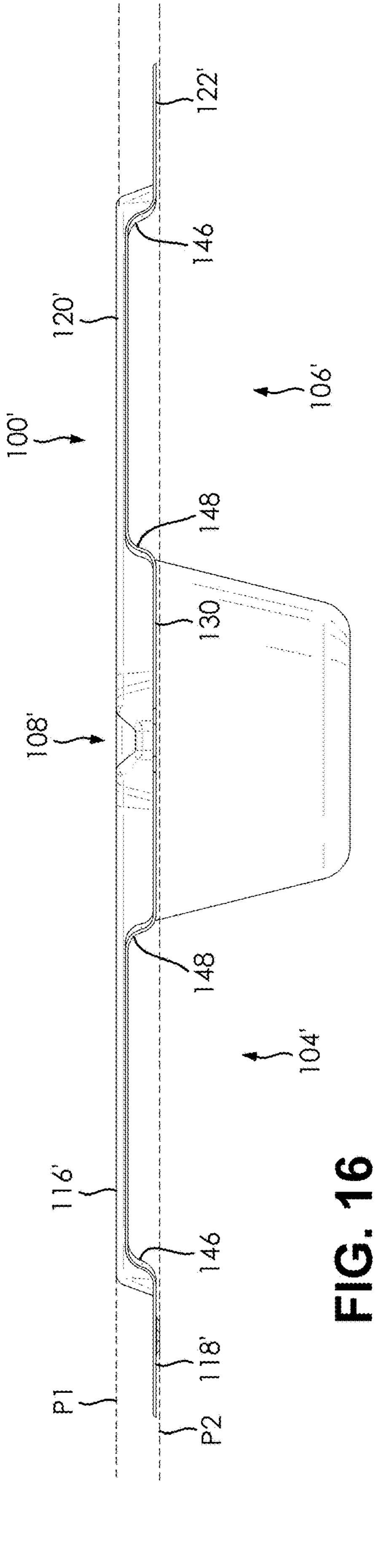
FIG. 16 is a front elevational view thereof.
Figure 17:
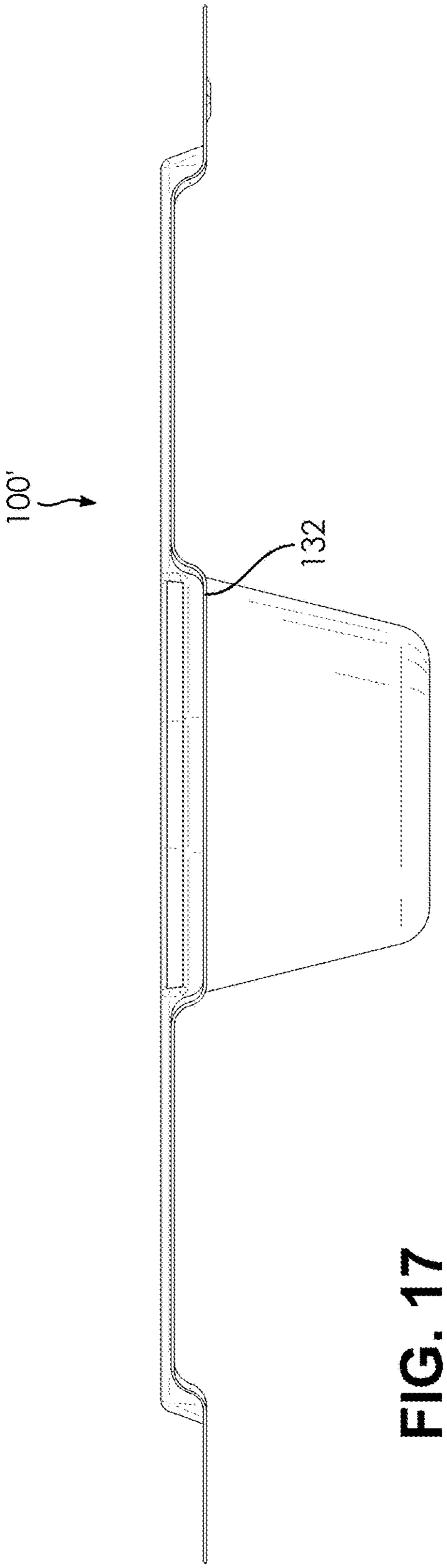
FIG. 17 is a rear elevational view thereof.
Figure 18:
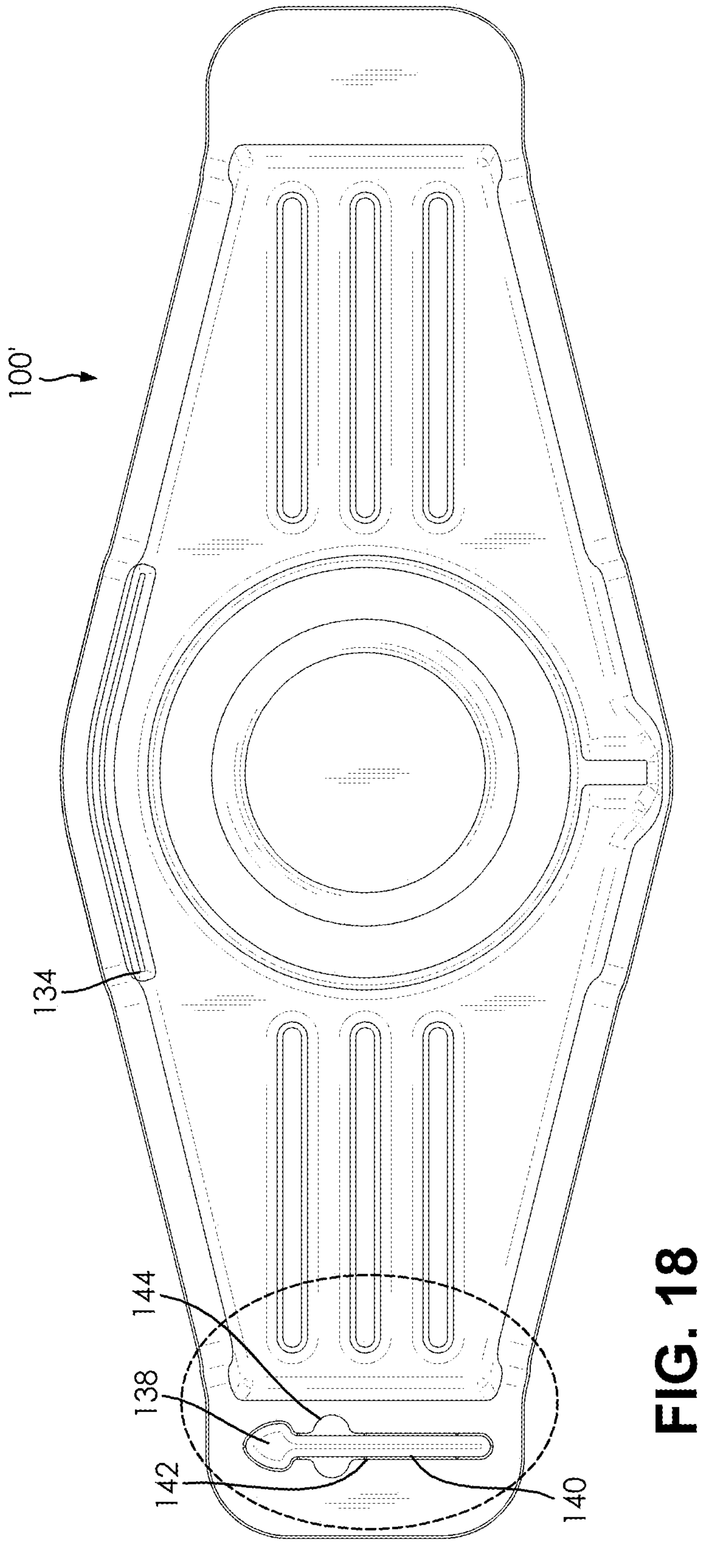
FIG. 18 is a top plan view thereof.
Figure 19:
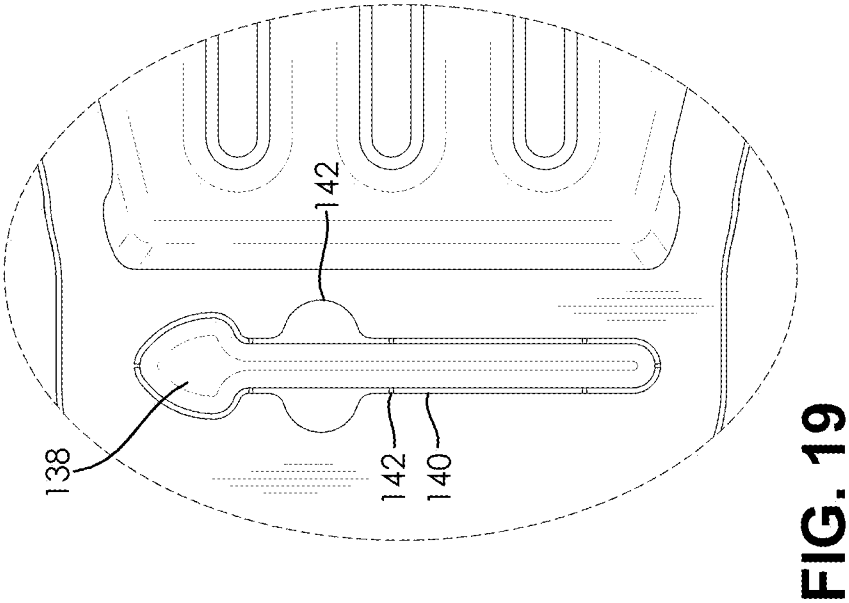
FIG. 19 is an enlarged top plan view, taken at the callout in FIG. 18 depicting a collection scoop.
Figure 20:
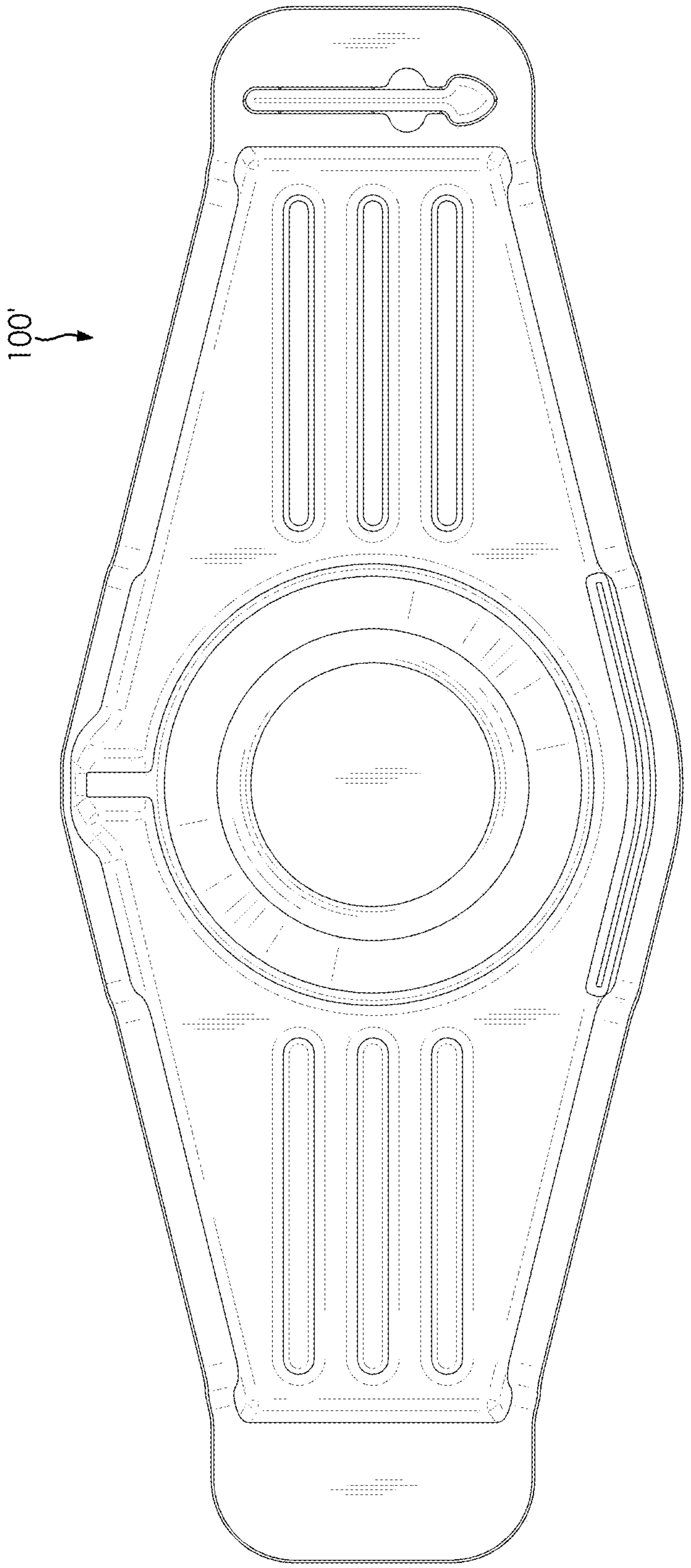
FIG. 20 is a bottom plan view of the collection container with scoop of FIG. 14.
Figure 22:
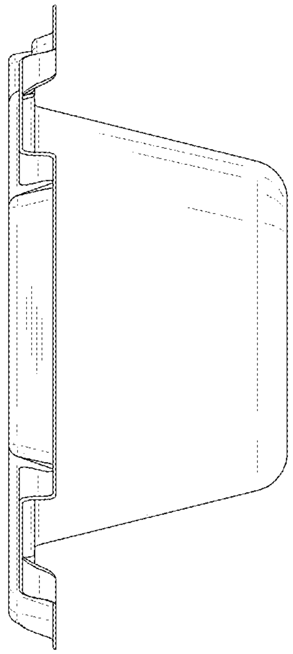
FIG. 22 is a right side elevational view thereof.
Figure 21:
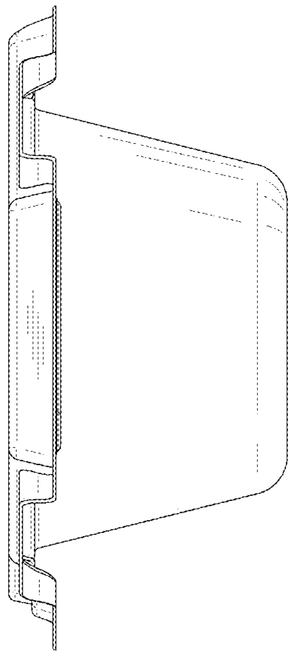
FIG. 21 is a left side elevational view thereof.

With particular reference to FIG. 16, the first arm 116', the second arm 120', and the central recess 108' can be disposed on a first plane (P1). The first handle 118 and the second handle 122' can be disposed on a second plane (P2) that is different plane than the plane of central recess 108', first arm 116', and first handle 118'. The second plane (P2) can be located vertically below the first plane (P1) when the collection container 100 is oriented in an operable position, for example, above a toilet bowl 103.

The first end 104', second end 106', and the central recess 108' can be generally circumscribed by a lip 128. The first handle 118' and the second handle 122' can be part of or co-formed with the lip 128. Portions of the lip 128 adjacent to the central recess 108 can be disposed on the second plane (P2). A first portion 130 of the lip 128 can be disposed adjacent to the pour spout 114'. A second portion 132 of the lip 128 can be disposed opposite the first portion 130 of the lip 128, with the central recess 108' disposed therebetween.

A support ridge 134 can be formed in an underside 129 of the collection container 100. In particular, the support ridge 134 can be formed adjacent to the second portion 132 of the lip 128. The support ridge 134 can span between the second plane (P2) and the first plane (P1) in a "stair-step fashion." Advantageously, this support ridge 134 can improve the overall rigidity of the collection container 100.

Figure 15:
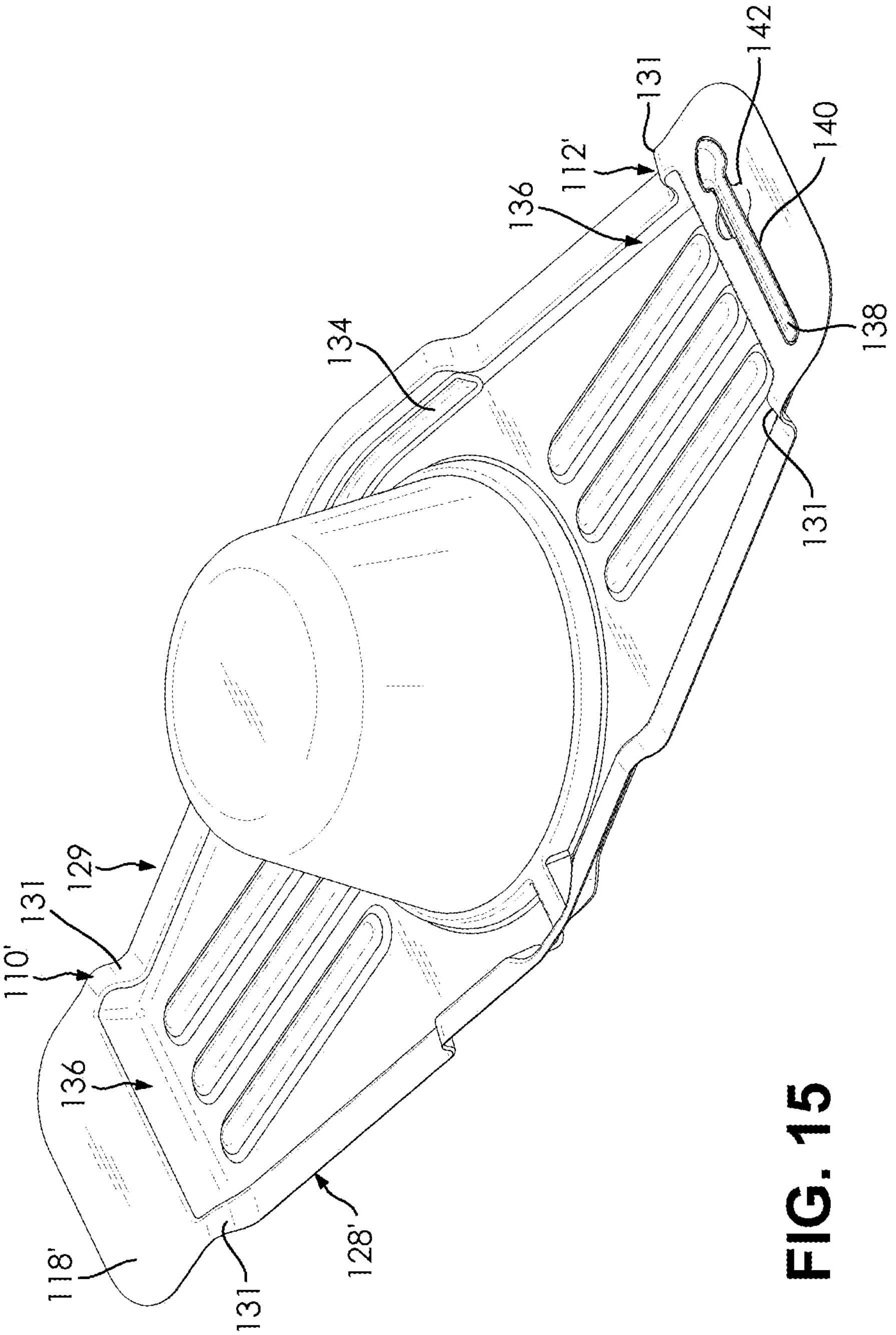
FIG. 15 is a bottom perspective view thereof.

The first stopper 110' and second stopper 112' can extend from the central recess 108' to each respective handle 118', 122'. The first stopper 110' and second stopper 112' have an exterior portion 146 and an interior portion 148. Each of the exterior portion 146 and the interior portion 148 can span between the first plane (P1) and the second plane (P2). As shown in FIG. 15, the exterior portion 146 of the first stopper 110' can be a wall formed between the first arm 116' and the first handle 118'. The exterior portion 146 of the second stopper 112' can be a wall formed between the second arm 120' and the second handle 122'. The interior portion 148 of each of the first stopper 110' and the second stopper 112' can be a wall formed adjacent to the central recess 108'. In certain embodiments, the exterior portion 146 first stopper 110' and the second stopper 112' can form walls disposed on opposite sides of the respective arms 116', 120'. In that way, the first stopper 110 and the second stopper 112' can each define a handle recess 136. The handle recesses 136 can be formed on an underside of the collection container 100' adjacent to the first handle 118' and second handle 122'. The handle recesses 136 can allow the user to grasp the first and second handles 118', 122' when the first and second stoppers 110', 112' are engaged on the toilet bowl 103. The first stopper 110' and the second stopper 112' can also include an interior portion adjacent to the central recess 108'. The interior portion can also span from the first plane (P1) to the second plane (P2).

The first stopper 110' and second stopper 112' can have an arcuate surface 131 with a curvature configured to match the curvature of the toilet bowl 103. The matching curvature of the arcuate surface 131 of each of the first stopper 110' and the second stopper 112' and the toilet bowl 103 can facilitate a more secure connection between each of the first stopper 110' and the second stopper 112' and the toilet bowl 103. Advantageously, the secure connection helps the collection container 100 remain in place on the toilet while in use further militating against possible mess. One of ordinary skill in the art can select a suitable curvature to match the curvature of the toilet bowl 103.

The first handle 118' of the collection container 100' can include a collection spoon 138, enhancing the functionality of the collection container by integrating a tool for sample retrieval directly from the collection container 100'. The collection spoon 138 can be integrally formed within the first handle 118'. It should be appreciated that in further embodiments, the collection spoon 138 can be positioned anywhere on the collection container 100'.

The collection spoon 138 can be formed and disposed into an aperture 140 within the first handle 118'. The aperture 140 can mirror the shape of the collection spoon 138. The aperture 140 can include finger grab holes 144 located between the body of the collection spoon 138 and the edges of the aperture 140. The finger grab holes 144 can provide adequate space for the fingers of the user, allowing for a firm grip and easy manipulation of the spoon when detaching it from the handle. The inclusion of the finger grab holes 144 not only aids in the ergonomic retrieval and handling of the spoon but also enhances the overall user experience by making the process of collecting a sample more efficient and hygienic.

The collection spoon 138 can be connected to the edges of the aperture 140 through a series of connection tabs 142. The connection tabs 142 can act as a temporary bonding agent, holding the collection spoon 138 in place within the spoon-shaped aperture 140. In practical operation, the user can access the collection spoon 138 by pulling it out from the first handle 118'. The connection tabs 144 can be robust enough to allow the collection spoon 138 to remain securely attached during normal handling and storage of the collection container 100, yet the connection tabs 144 can be thin enough to allow the user to break them with a simple, intentional pull. This allows the collection spoon 138 to be detached without the need for additional tools or excessive force. The collection spoon 138 and the connection tabs 142 can be integrally formed with the collection container 100, where the entirety of the collection container 100 is formed from a single piece of material by injection molding or vacuum molding, for example. In further embodiments, the collection spoon 138 can be connected to the collection container 100' through other attachment means, such as hinges, perforation, and adhesive as non-limiting examples. A skilled artisan can select an appropriate attachment means for the collection spoon 138 within the scope of the present disclosure.

It should be appreciated that the collection container 100 of the present disclosure can be configured to be positioned at various locations on the toilet bowl 103 and for various sizes and shapes of toilet bowls 103, in operation. Advantageously, the collection container 100 described herein can create a stable attachment with a toilet bowl 103 and allow the user to deposit a sample 101 without mess. Further, the sample 101 collection kit including the collection container 100 and sample 101 cup can allow for the user to collect a stool sample 101 without contamination and mess. The present disclosure provides ways to facilitate easier stool collection by a patient, protect the sample 101 from biocontamination, and enable easier sample 101 disbursement into collection receptacles by a patient or lab technician. These aspects can improve patient compliance and thereby make diagnostic data more readily available for patients, diagnostic centers, clinicians, and labs.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A collection container comprising:

a unitary body including a first end and a second end;

a central recess disposed between the first end and the second end;

a first arm including a first handle, the first arm extending between the first end and the central recess, and a collection spoon disposed on the first arm;

a second arm including a second handle, the second arm extending between the second end and the central recess;

a lip circumscribing the first end, the second end, and the central recess; and a support ridge formed on an underside of the collection container adjacent to the central recess.

2. The collection container of claim 1, wherein the collection spoon is integrally formed within the first handle.

3. The collection container of claim 1, wherein the collection spoon is disposed in a spoon-shaped aperture in the first handle.

4. The collection container of claim 3, wherein the collection spoon is detachably connected to an edge of the spoon-shaped aperture by a connection tab.

5. The collection container of claim 3, wherein a finger grab hole is formed between the collection spoon and an edge of the aperture.

6. A collection container comprising:

a unitary body including a first end and a second end;

a central recess disposed between the first end and the second end;

a first arm including a first handle, the first arm extending between the first end and the central recess, and a collection spoon disposed on the first arm;

a second arm including a second handle, the second arm extending between the second end and the central recess, wherein the first arm and the second arm are disposed on a first plane, the first handle and the second handle are disposed on a second plane, and the first plane is different from the second plane; and a first stopper and a second stopper, each of the first stopper and the second stopper including an arcuate surface with a curvature configured to match a curvature of a toilet bowl.

7. The collection container of claim 6, wherein the first stopper includes an exterior portion adjacent to the first handle and an interior portion adjacent to the central recess.

8. The collection container of claim 7, wherein the second stopper includes an exterior portion adjacent to the second handle and an interior portion adjacent to the central recess.

9. The collection container of claim 7, wherein the exterior portion defines a handle recess on an underside of the collection container adjacent to the first handle.

10. The collection container of claim 6, further comprising a support ridge formed on an underside of the collection container adjacent to the central recess.

11. The collection container of claim 10, wherein the support ridge is formed adjacent to the central recess.

12. The collection container of claim 6, wherein the collection spoon is integrally formed within the first handle.

13. The collection container of claim 12, wherein the collection spoon is disposed in a spoon-shaped aperture in the first handle.

14. The collection container of claim 13, wherein the collection spoon is detachably connected to an edge of the spoon-shaped aperture by a connection tab.

15. The collection container of claim 13, wherein finger grab holes are defined between the collection spoon and an edge of the aperture.

* * * * *